United States Patent

Tanaka et al.

[11] Patent Number: 5,586,975
[45] Date of Patent: Dec. 24, 1996

[54] AIR AND LIQUID TIGHT CONTAINER WITH A SLIDABLE GASKET

[75] Inventors: Nobuo Tanaka, Mishima-gun; Seiji Otani, Toyono-gun; Hiroyuki Kawakita, Suita; Teruo Matsuda, Chiyoda-ku, all of Japan

[73] Assignees: Takeda Chemical Industries. Ltd., Osaka; Arte Corporation, Tokyo, both of Japan

[21] Appl. No.: 365,947

[22] Filed: Dec. 29, 1994

[30] Foreign Application Priority Data

Feb. 18, 1994 [JP] Japan .................................... 6-021485

[51] Int. Cl.$^6$ .................................................... A61M 37/00
[52] U.S. Cl. .............................. 604/89; 604/191; 604/218
[58] Field of Search .............................. 604/238, 82, 89, 604/90, 92, 191, 218, 238, 181, 187, 219, 220, 221, 224, 225, 230

[56] References Cited

U.S. PATENT DOCUMENTS

| | | |
|---|---|---|
| Re. 34,845 | 1/1995 | Vetter et al. .................. 604/82 |
| 1,961,023 | 5/1934 | West .......................... 604/230 |
| 2,688,967 | 9/1954 | Huber . |
| 3,330,282 | 7/1967 | Visser et al. ................. 604/90 |
| 3,807,119 | 4/1974 | Shields . |
| 3,967,759 | 7/1976 | Baldwin et al. . |
| 4,067,333 | 1/1978 | Reinhardt et al. . |
| 4,235,235 | 11/1980 | Bekkering . |
| 4,303,070 | 12/1981 | Ichikawa et al. ............. 604/222 X |
| 4,424,057 | 1/1984 | House . |
| 4,439,184 | 3/1984 | Wheeler .................... 604/191 |
| 4,496,344 | 1/1985 | Kamstra . |
| 4,599,082 | 7/1986 | Grimard ..................... 604/90 |
| 4,613,326 | 9/1986 | Szwarc ...................... 604/89 |
| 4,668,223 | 5/1987 | Grotenhuis . |
| 4,792,329 | 12/1988 | Schreuder . |
| 4,820,286 | 4/1989 | van der Wal . |
| 4,822,340 | 4/1989 | Kamstra . |
| 4,874,381 | 10/1989 | Vetter . |
| 4,968,299 | 11/1990 | Ahlstrand et al. . |
| 5,069,670 | 12/1991 | Vetter et al. . |
| 5,080,649 | 1/1992 | Vetter . |
| 5,139,490 | 8/1992 | Vetter et al. . |
| 5,383,864 | 1/1995 | van den Heuvel .............. 604/218 |

FOREIGN PATENT DOCUMENTS

| | | |
|---|---|---|
| 0311324A2 | 10/1988 | European Pat. Off. . |
| 0311324A3 | 10/1988 | European Pat. Off. . |
| 0360313A1 | 8/1989 | European Pat. Off. . |
| 75 06745 | 3/1975 | France . |
| 1616199 | 5/1972 | Germany . |
| 2258373 | 6/1973 | Germany . |
| 3924830 | 7/1989 | Germany ..................... 604/89 |
| 705392 | 3/1954 | United Kingdom . |

*Primary Examiner*—Corrine M. McDermott
*Assistant Examiner*—N. Kent Gring
*Attorney, Agent, or Firm*—Wenderoth, Lind & Ponack

[57] ABSTRACT

An air and liquid-tight container is capable of storing different substances in different compartments sealingly separated by a front gasket having two separate parts that are independently slidable. A rear gasket is connectable to a push rod so as to function as a plunger, the front gasket being slidable in response to sliding of the rear gasket, thereby enabling the substance in the rear compartment to be introduced into the front compartment through a bypass. The front and rear gaskets are encased in the tubular body at a compressibility C (%) of 2% to 10%, with the product of the compressibility and the contact area (mm$^2$) of the gaskets with the inside wall of the tubular wall falling within the range of 150 to 400.

10 Claims, 3 Drawing Sheets

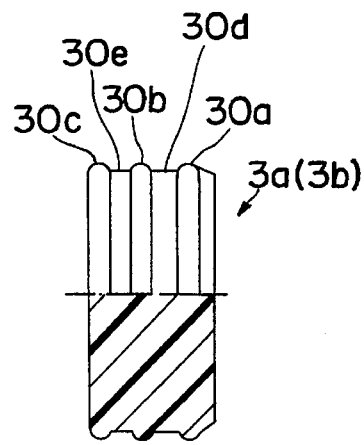
F I G. 7(A)
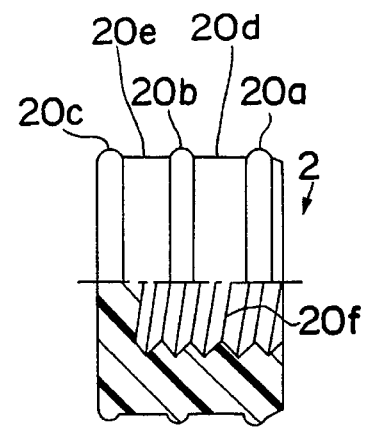
F I G. 7(B)
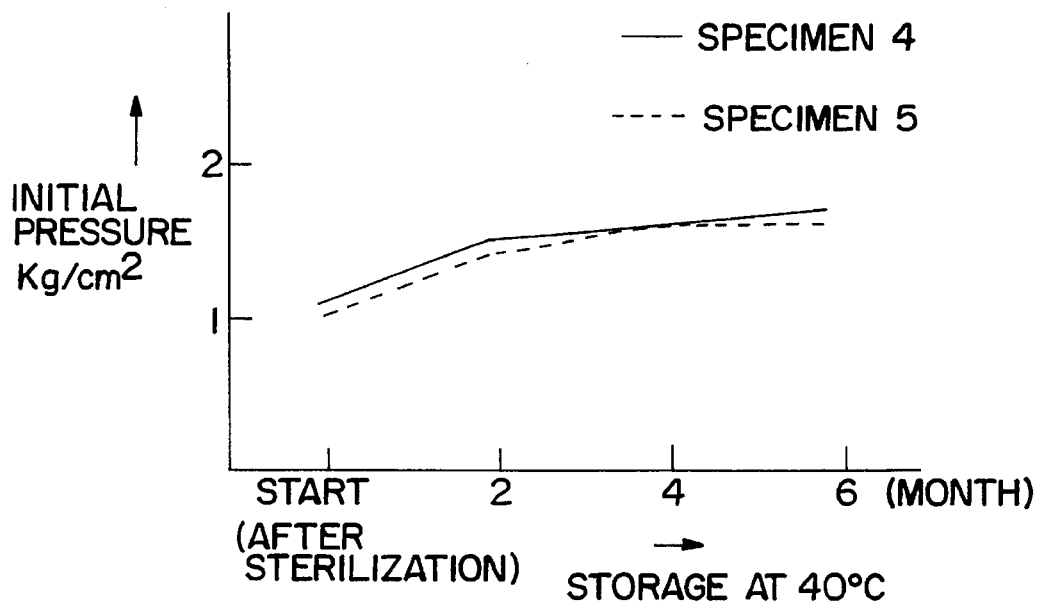
F I G. 8

AIR AND LIQUID TIGHT CONTAINER WITH A SLIDABLE GASKET

FIELD OF THE INVENTION

The present invention relates to an air and liquid-tight container capable of storing different substances in different compartments sealingly separated by a front gasket having two parts that are independently slidable, and a rear gasket which functions as a plunger by axially sliding by means of a push rod detachably connected thereto, thereby enabling the front gasket to slide axially in the container. Hereinafter, the rear gasket will be referred to as a "plunger".

BACKGROUND OF THE INVENTION

A typical example of containers of this kind is a syringe, commonly called "prefilled syringe," which can be loaded with two different substances placed in different compartments, and allows the substances to mix through a bypass under the movement of the gaskets effected by a plunger slidably inserted in one end of the tubular body.

More particularly, in the case of a syringe a liquid medicinal substance is filled in one of the compartments, and then it is freeze-dried into a powdery state. The other substance is a vehicle placed in the other compartment, which is used to dissolve or disperse the powdery medicinal substance. In this way a prefilled syringe is finished. In most cases, the vehicle is sterilized by steam after the tubular body is sealed. The problem arises that the steam serialization is likely to denature the prefilled medicinal substance. To avoid this problem, the medicinal substance is placed after the steam sterilization is completed. This method causes another problem in that moisture from the steam is likely to stay on the gasket and impregnate the gasket or penetrate therethrough, thereby spoiling the desiccated medicinal substance with the moisture.

In order to solve the problem of moisture, there is a proposal for heating the syringe at 100° C. or more for hours so as to dry the moisture, but this high temperature is likely to spoil the vehicle.

In conclusion, the problems of moisture arise from the single structure of the gasket which separates the space into the two compartments.

In order to solve the problems, there is an improved prefilled syringe which is disclosed in EPC Publication No. 0 568 321 A 2. The syringe is provided with a double-structure gasket used for separating the interior space of the tubular body into a front compartment and a rear compartment in a sealing manner. The double-structure gasket refers to a gasket consisting of two parts which are slidable independently of each other. For explanation's sake, the two gasket parts will be referred to as a "front part" and a "rear part".

Because of the presence of a possible gap between the two parts, even after steam sterilization is finished, moisture likely to remain in and on the rear part is prevented from reaching the front part and wetting it.

Each gasket includes annular ribs sealingly engaging the inside wall of the tubular body. Preferably it is additionally provided with bridging ribs extending between the adjacent annular ribs and subdividing a space between the annular ribs. The bridging ribs also sealingly engage the inside wall of the tubular body wherein "sealingly engage" does not always mean that the bridging ribs are compressed against the inside wall of the tubular body.

However, it has been found that it is difficult to ensure that all the annular ribs of the two parts sealingly engage the inside wall of the tubular body at equal pressure. If the contact pressure is not equal, the parts fail to effect an air and liquid thight seal. However, the air and liquid-tight seal and slidability of the parts are mutually contradictory; if the gasket is too tight against the inside wall of the tubular body, it slides on it with difficulty, whereas if it is loose, the gasket can easily slide, but the air and liquid tight seal will be sacrificed.

The compressibility of a gasket can be expressed by the following equation:

$$C (\%) = \frac{R-r}{R} \times 100 \qquad (1)$$

where R (mm) is the outside diameter of the annular ribs of the gasket which stands out of the tubular body, being subject to no compression, and r (mm) is the inside diameter of the tubular body.

Japanese Patent Publication (allowed) No. 57-26782 discloses a syringe having a gasket encased therein which is superior in slidability and air and liquid-tight seal. The gasket is made of thermoplastic elastomer whose annular ribs have a compressibility C of 0.6 to 18.3% depending upon the inside diameter of the syringe. In addition, the product of the total contact area S ($mm^2$) and compressibility (C) is in the range of about 350 to about 900.

Japanese Utility Model Laid-Open Publication No. 3-63344 discloses a gasket having annular ribs at least one of which has a contact area S of 28 $mm^2$ or more as well as a compressibility C of 1 to 5. The product of the compressibility (C) and the contact area (S) is set so as to fall within the range of about 100 to about 250.

However, problems are likely to arise in these known gaskets when they are used in association with prefilled syringes, because the gaskets are fabricated without taking into consideration any unfavorable influences likely to rise from pre-treatments such as freeze-drying and steam sterilization applied to the syringes or from storage. In encasing the gaskets in prefilled syringes, a likely deformation thereof must be taken into consideration.

The prior art gaskets referred to above are fabricated without taking into consideration possible compression deformation.

More specifically, the Publication No. 57-26782 teaches that for medical purposes the syringe is sterilized with the gasket encased therein using ethylene oxide gas at a temperature of about 60° to about 65° C. for about 6 to 8 hours and recognizes that the compressibility is adequate if it falls in the range of 0.6 to 18.3%. However this prior art literature does not refer to deformation likely to occur when the syringe is freeze-dried or stored for a long time. In addition, it is necessary to make the gasket with a special type of having an optimum C×S value so as to improve the slidability.

Another prior art Publication No. 3-63344 does not teach any counteraction against unfavorable influences upon the slidability and liquid-tightness of the syringe when they are freeze-dried and stored over a long time.

SUMMARY OF THE INVENTION

The present invention is directed to solve the problems pointed out above with respect to the prior art and provides an air and liquid-tight container using one or more slidable gaskets which are capable of maintaining slidability and fit regardless of pre-treatment such as sterilizing and freeze-drying and a long period of storage, the gasket being advantageously made of a common material.

According to one aspect of the present invention, there is provided an air and liquid-tight container which includes a tubular body having a front open end and a rear open end and a front gasket slidable in the tubular body. The front gasket separates the inside space of the tubular body into a front compartment and a rear compartment, each of the compartments having a substance therein. A rear gasket is connectable to a push rod so as to function as a plunger, the front gasket is slidable in the tubular body in response to sliding of the rear gasket, and a bypass is located between the front gasket and the front open end having an axial length along the tubular body. The bypass permits the substance in the rear compartment to be introduced into the front compartment. The front gasket comprises a front part and a rear part axially slidable independently of each other upon sliding of the rear gasket in the tubular body by the push rod. Each of the front and rear gaskets comprises an annular rib sealingly engaging the inside wall of the tubular body, and the front and rear gaskets are encased in the tubular body such that the compressibility C (%) of the ribs is in a range from 2% to 10%, inclusive, and the product of the compressibility and the contact area (mm$^2$) of the ribs with the inside wall of the tubular body is in a range of 150 to 400.

According to another aspect of the present invention, there is provided an air and liquid-tight container which includes a tubular body having a front open end and a rear open end, a front gasket slidable in the tubular body, the front gasket separating the inside space of the tubular body into a front compartment and a rear compartment, and each of the compartments having a substance therein, a rear gasket connectable to a push rod so as to function as a plunger. The front gasket is slidable in the tubular body in response to sliding of the rear gasket. A bypass between the front gasket and the front open end has an axial length along the tubular body, the bypass permitting the substance in the rear compartment to be introduced into the front compartment. The front gasket comprises a front part and a rear part axially slidable independently of each other upon sliding of the rear gasket in the tubular body by the push rod. Each of the front and rear gaskets comprises annular and bridging ribs located thereon and sealingly engaging the inside wall of the tubular body, the annular ribs having a space therebetween and the bridging ribs extending between the annular ribs and subdividing the space between the annular ribs. The front and rear gaskets are encased in the tubular body such that the compressibility C (%) of the ribs is in a range from 2% to 10%, inclusive, and the product of the compressibility and the contact area (mm$^2$) of the ribs with the inside wall of the tubular wall is in a range of 150 to 400.

In general, the inside diameter of a container and the fit of a gasket against the container are related as shown in Table 1, wherein the "fit" is a fitting degree expressed in terms of a difference between the maximum outside diameter R (mm) of the part 3$a$ (3$b$) and of the plunger 2 and the inside diameter r (mm) of the tubular body 1:

TABLE 1

| FIT | INSIDE DIAMETER (mm) | | | | | |
|---|---|---|---|---|---|---|
| | 8 | 10 | 12 | 14 | 16 | 18 |
| 0.1 (mm) | 2.44 | 1.96 | 1.64 | 1.41 | 1.23 | 1.10 |
| 0.2 | 4.76 | 3.85 | 3.22 | 2.78 | 2.44 | 2.17 |
| 0.3 | 6.98 | 5.66 | 4.76 | 4.11 | 3.61 | 3.22 |

TABLE 1-continued

| FIT | INSIDE DIAMETER (mm) | | | | | |
|---|---|---|---|---|---|---|
| | 8 | 10 | 12 | 14 | 16 | 18 |
| 0.4 | 9.01 | 7.41 | 6.25 | 5.41 | 4.76 | 4.25 |
| 0.5 | 11.11 | 9.09 | 7.69 | 6.67 | 5.88 | 5.26 |

It will be understood from Table 1 that the diameter of a container is inversely proportional to the fit of a gasket, which means that as the container becomes small, the compressibility of the gasket increases, and vice versa. On the basis of the data shown in Table 1, the compressibility C of the ribs should be in the range of 2% to 10%, preferably 4% to 7%, wherein 2% presupposes that the container is large and 10% presupposes that it is small. If the lower limit is below 2%, the air and liquid-tightness will be sacrificed while proper slidability is kept. If the upper limit is above 10%, slidability will decrease while proper tightness is kept.

The container is cylindrical, with the same diameter throughout its entire length, and in addition to the gasket and plunger referred to above, a further gasket is provided to plug the front end. Taking this plug (gasket) into account, the total number of gaskets will amount to four. When two to four gaskets are encased in the tubular body, it is arranged such that the product of the compressibility (%) and the whole contact area (mm$^2$) of the annular ribs of all the gaskets with the inside all of the tubular body may be in the range of about 300 to about 1200, preferably 400 to 900. The lower limit "about 300" presupposes that the container has a small inside diameter, and the upper limit "about 200" presupposes that the container has a large inside diameter.

In operation, as a first step the rear gasket is pushed into the tubular body by means of the push rod, thereby enabling the front gasket to move into the depth of the tubular body, the rear gasket functioning as a plunger. As a second step, during the movement of the front gasket a substance in the rear compartment is introduced into the front compartment containing another substance through the bypass. At this stage, the container may be shaken to mix the two substances in the front compartment to obtain a homogeneous mixture. Then the plunger (rear gasket) is advanced into the depth of the tubular body until the mixture is ejected through an opposite end of the container.

BRIEF DESCRIPTION OF THE DRAWINGS

FIG. 1 is a schematic cross-sectional view through an embodiment of the present invention;

FIGS. 2(A) and 2(B) show a process of assembling a container of the embodiment of FIG. 1, wherein FIG. 2(A) shows a first step in which a substance in a rear compartment is introduced into a front compartment;

FIGS. 7(A) and 7(B) show a schematic view on an enlarge scale of a modified version of the gaskets; and FIG. 8 is a graph depicting the relationship between initial pressures and storage over a given period of time.

DETAILED DESCRIPTION OF THE PREFERRED EMBODIMENT

Figure 3:
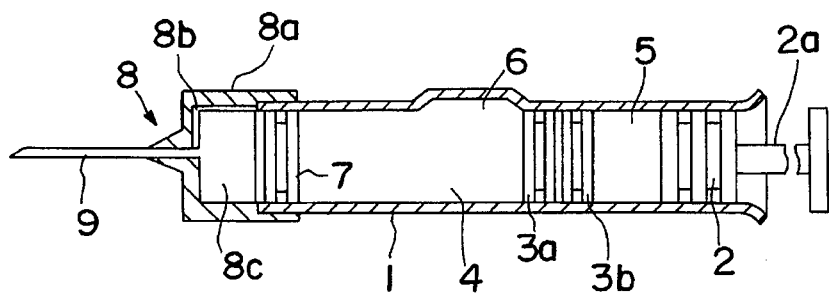
FIG. 3 is a cross-section through the container shown in FIG. 1, which is provided with a cap having a needle for use as a syringe.

The container according to the present invention will be described in detail by taking a prefilled syringe as a typical example.

Referring to FIG. 1, an exemplary prefilled syringe has a generally tubular body 1 having the same diameter throughout its entire length and which is open at the front and rear ends. The syringe is provided with another gasket, that is, a plunger 2 connectable to a push rod 2a slidably inserted into the body 1 through the rear end. The body 1 includes a first (front) compartment 4 and a second (rear) compartment 5 separated by a gasket 3, which consists of a front part 3a and a rear part 3b. The gasket 3 as a unit is slidable in and along the body 1 under pressure provided by the plunger 2. The first compartment 4 stores a medicinal component P (illustrated in a powder form) and the second compartment 5 stores a vehicle L in a liquid or any other form for dissolving or dispersing the medicinal component P, or for becoming mixed therewith. The reference numeral 6 denotes a bypass in the form of an axially extending recess through which the vehicle L is introduced from the compartment 5 into the compartment 4. The gasket 3 and plunger 2 can be made of normal isobutylene-isoprene rubber, halogenide butylene rubber, butadiene rubber, isoprene rubber or chlorinated isobytylene-isoprene rubber or a mixture thereof.

The front part 3a and the rear part 3b of the gasket 3 are independent of each other and separately movable. Each of the parts 3a and 3b extends radially to the inside wall of the body 1 to seal the rear compartment 5 from the front compartment 4. The combined axial length of the parts 3a and 3b is less than the axial length of the bypass 6 to permit the injection liquid to be transferred from the rear compartment 5 to the front compartment 4. When the parts 3a and 3b are between the bypass 6 and the rear end of the tubular body 1, they preferably engage each other, but they can be slightly spaced because of air being compressed therebetween. In use, as the plunger 2 is initially pushed by means of the push rod 2a, the air present between the parts 3a and 3b is compressed by the movement of the rear part 3b. This compression urges the front part 3a forward until the rear face of the front part 3a reaches the bypass 6, whereupon any air between the parts 3a and 3b escapes therefrom to the bypass 6 to permit the parts 3a and 3b to engage each other if not already. In this engaged state the gasket parts 3a and 3b travel along the remainder of the tubular body 1. The front end portion of the body 1 is closed by a movable plug 7; the illustrated example is a syringe, so that as shown in FIG. 3 a cap 8 carrying an injection needle 9 is used.

Figure 4:
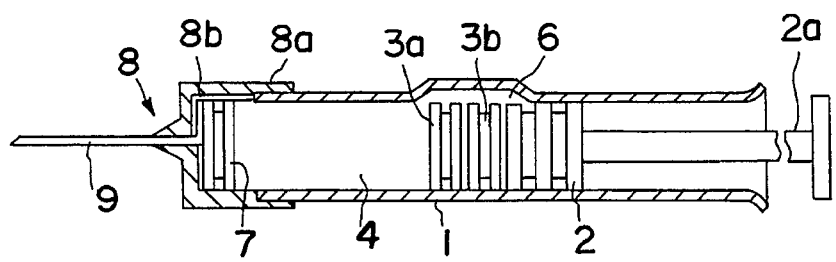
FIG. 4 is a cross-section through the syringe shown in FIG. 1 particularly showing the dimensional relationship between the bypass and the front gasket.

The bypass 6 has a length longer than the total thickness of the front part 3a and the rear part 3b, as shown in FIG. 4. Furthermore, the combined axial length of the parts 3a, 3b, and the plunger 2 (exclusive of the push rod 2a) is greater than the axial length of the bypass 6 to prevent backflow of air or liquid from the front compartment 4 to the rear compartment 5.

The plunger 2 is pushed to the left (FIG. 1) whereby the front part 3a and rear part 3b of the gasket 3 are moved together in a spaced apart fashion under pressure provided by the plunger 2. When the parts 3a and 3b reach the bypass 6 as shown in FIG. 4, the vehicle L in the rear compartment 5 is introduced into the front compartment 4 through the bypass 6, thereby effecting a desired section such as dispersing, dissolving or mixing between the medicinal component P and the vehicle L. In this way an injecting medicine (or simply an injection) is obtained in the front compartment 4. By further pushing the plunger 2, the mixture in the tubular body 1 can be ejected through the injection needle 9.

The prefilled syringe is assembled as shown in FIGS 2A and 2B:

Referring to FIG. 2A, the rear part 3b of the gasket 3 is inserted in the body 1 and the vehicle L is put in the rear compartment 5. Then the plunger 2 is inserted. The vehicle L is heat sterilized by dry steam, and then the inside surface of the front compartment 5 is air-dried typically with some heat (some example, up to 50°-60° C.) as long as such heat does not damage the vehicle L in the rear compartment 5. During the step of sterilization, the outer ends of the rear part 3b and plunger 2 are exposed to the dry steam and may absorb or take in moisture, which may diffuse into the rear part 3b or plunger 2. This moisture, over a period of time, may escape by diffusion or some other means out of the end of the rear part 3b or plunger 2 into which it entered. This emanating moisture could then adversely affect a hygroscopic powder contained in the front compartment 4.

After the front compartment 4 has been dried as shown in FIG. 2B, the front part 3a of the gasket 3 which is kept away from any moisture, is inserted into the body 1 through the front end 1a until it comes relatively near to or into contact with the rear part 3b so as to be adjacent thereto. A dose of powder medicinal component P is placed in the front compartment 4, and then the front end 1a is closed by the plug 7. In this way a finished syringe is obtained.

When the vehicle L is sterilized by dry steam, the rear part 3b the gasket 3 becomes wet because of the deposition of dew, or saturated with moisture. Although most of this moisture is removed when the front compartment 4 is dried, some of it remains in the rear part 3b, only to diffuse out over a period of time. The front part 3a is kept dry, thereby sealing the front compartment 4 against any moisture which may escape from the rear part 3b.

The injection needle 9 can be fixed to the syringe 1 in various ways, one example being shown in FIG. 3.

The example shown in FIG. 3 has the front end 1a capped with a cap 8 which includes a skirt 8a carrying the injection needle 9. The skirt 8a includes a groove 8b on its inside surface. The groove 8b communicates with the needle 9. The reference numeral 8c denotes space adapted to receive the plug 7 as shown in FIG. 4.

When the plunger 2 is pushed to the left (FIG. 4), the plug 7 is moved into the space 8c, and the vehicle L in the rear compartment 5 is introduced into the front compartment 4 through the bypass 6. By further pushing the plunger 2 and after the syringe is shaken or swung to mix the liquid and drug, the injection is introduced into the needle 9 through the groove 8b. The needle 9 may b fixed to the cap 8 beforehand, or it may be fixed after the cap 8 is capped to the syringe 1.

Figure 5:
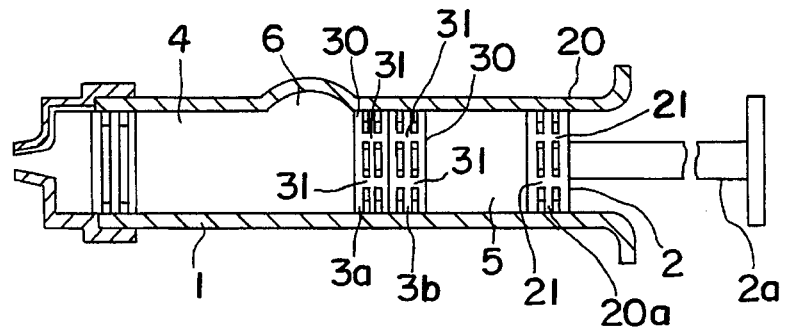
FIG. 5 is a cross-section through a modified version of the embodiment.
Figure 6:
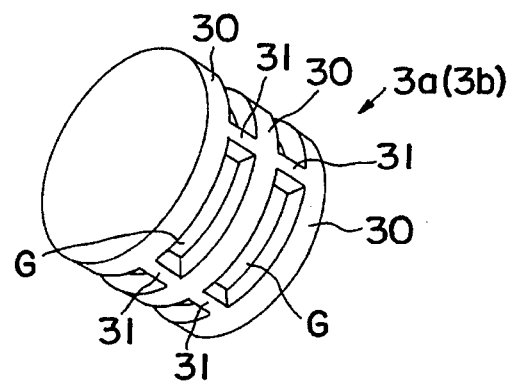
FIG. 6 is a perspective view showing the gaskets used in the modified version shown in FIG. 5.
Figure 3:
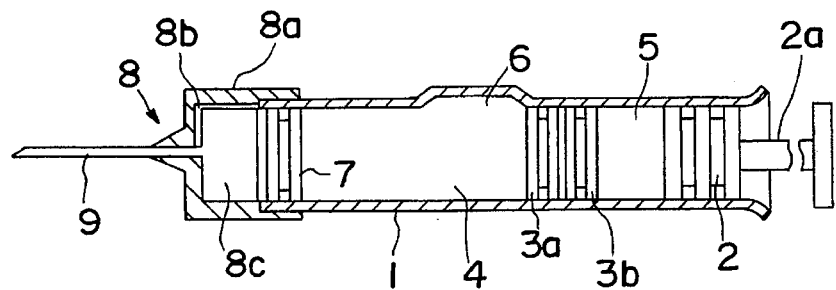
Figure 4:
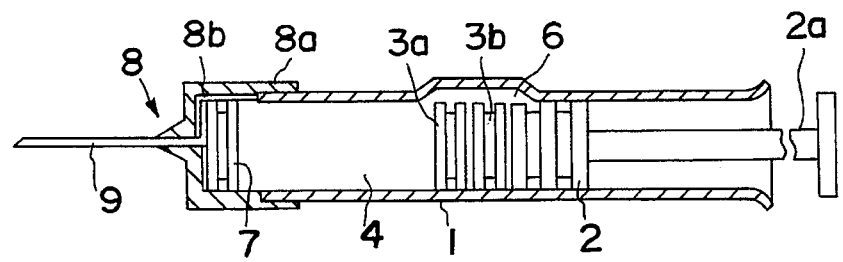
Figure 5:
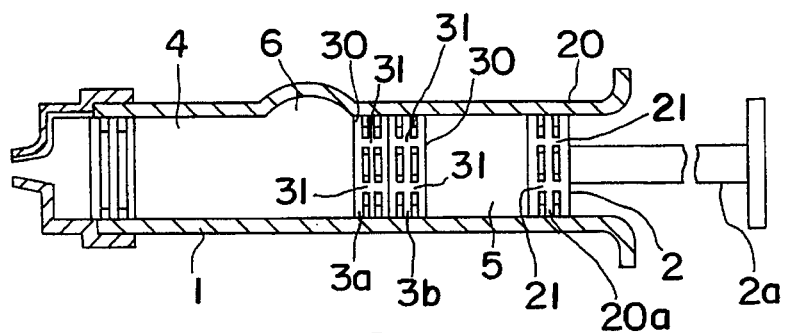
Figure 6:
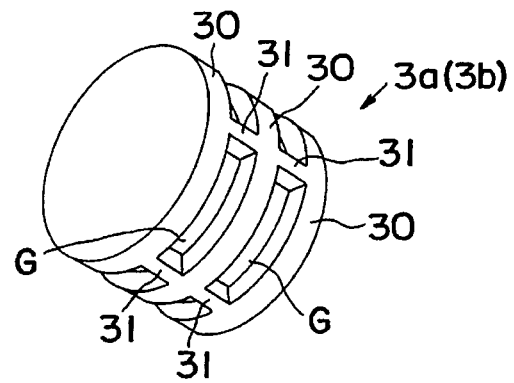

Referring to FIGS. 5 and 6, the gasket 3 is provided with a plurality of annular ribs 30 having grooves (G) therebetween. The adjacent grooves (G) are bridged by other ribs 31, which will be referred to as bridging ribs. The bridging ribs 31 may have the same height as that the annular ribs 30, or may have a slightly shorter height. The bridging ribs 31 subdivide the grooves (G) into separate small recesses. The illustrated part 3a and 3b have two grooves in parallel which are respectively bridged, by four bridging ribs 31 displaced at 90°, thereby obtaining eight equally divided recesses in all. The annular ribs 30 extend at generally a right angle to the axis of the tubular body 1 and the bridging ribs 31.

The subdividing of the grooves (G) by the bridging ribs 31 minimizes the amount of injection liquid remaining in the groove (G), thereby minimizing the amount of injection liquid which remains unused. The greater the number of bridging ribs which are used, the less the amount of injection liquid which remains unused, but as the number of the bridging ribs increases, the friction created between the gasket 3 and the inside wall of the tubular body 1 increases, thereby preventing smooth movement of the gasket 3 in the tubular body 1. The bridging ribs 31 act as barriers to prevent the injection liquid from flowing circumferentially about the gasket 3. Hence a lesser quantity of injection liquid is trapped in the annular grooves (G).

Referring to FIGS. 7(A) and 7(B), the exemplary part 3a and plunger 2 are respectively provided with annular ribs 30a, 30b, and 30c, and 20a, 20b, and 20c, with grooves 30e and 30d and 20e and 20d between the adjacent ribs. Since the part 3b has the same structure as the part 3a, the description thereof is omitted for simplicity. The parts 3a and the plunger 2 are fabricated such that the outside diameter of each annular rib is slightly larger than the inside diameter of the tubular body 1 when they are not encased in the body 1. when they are pressed into the container, the annular ribs sealingly engage the inside wall of the tubular body 1.

Preferably, each of the gaskets 3 and plunger 2 is provided with tapered shoulders at the right-hand sides, toward the rear end of the body 1, as shown in FIGS. 7(A) and 7(B). the illustrated part 3 is thinner than the plunger 2, which may be provided with a threaded bore 20f for accepting the push rod 2a.

As pointed out above, a problem is that seal and slidability of the gaskets are mutually contradictory; when the seal is good, slidability becomes poor, and vice versa.

In order to insure seal between the gaskets 3 and the plunger 2 and tubular body 1 without sacrificing slidability, five tests were conducted on five specimens to examine and establish any relationship between compressibility and the contact area of the annular ribs wit the inside wall of the tubular body 1. Table 2 shows data obtained from the tests:

TABLE 2

|  | Fit | (radius) C | (C × S) | (C × St) |
|---|---|---|---|---|
| Case I |  |  |  |  |
| Specimen 1 | 0.25 mm | 4.76 | 159 | 318 |
| Specimen 2 | 0.36 mm | 6.86 | 223 | 446 |
| Specimen 3 | 0.36 mm | 6.86 | 452 | 904 |
| Case II |  |  |  |  |
| Specimen 4 | 0.25 mm | 3.57 | 172 | 344 |
| Specimen 5 | 0.36 mm | 5.14 | 261 | 522 |

Case I and CASE II show situations with different containers having different inside diameters; that is, 10.5 mm and 14.0 mm were used. The "fit" is expressed in terms of a difference between the maximum outside diameter R (mm) of the part 3a (3b) and of the plunger 2 and the inside diameter r (mm) of the tubular body 1. The values are indicated by a radius portion (½ the value of the diameter). The compressibility (%) "C" is obtained by the formula (1), and the contact area (mm$^2$) "S" of each annular rib 30 and 20 with the tubular body 1, is obtained by the following formula (2). "St" is a total contact area (mm$^2$):

$$S(mm^2) = \pi r (d1 + d2 + \ldots dn) \quad (2)$$

where d1, d2, . . . dn is a with of each annular rib 30 and 20 at which each rib keeps contact with the inside wall of the body 1.

As shown in Table 2, the compressibility (C) is appropriately in the range of 3% to 7%, (C×S) is appropriately in the range of 160 to 450, and (C×St) is appropriately in the range of 300 to 900.

A group of baskets 3 and plungers 2 (Group I) were made of normal isobutylene-isoprene rubber and a second group of them (Group II) were made of chlorinated isobutylene-isoprene rubber, both in such a manner as to satisfy the values in the prescribed ranges. Then they were encased in the tubular body 1 and sterilized by an autoclave at 121° C. for 20 minutes. The air-tightness was measured, the results of which are shown in Table 3. Table 3 shows the assessments in terms of ○ and △ on seal achieved by each specimen prior to and subsequent to steam-sterilization, wherein the mark ○ represents "sealed", and the mark △ represents "probable leakage":

TABLE 3

|  | GROUP I | | GROUP II | |
|---|---|---|---|---|
| Time | I | II | I | II |
| Specimen 1 | ○ | △ | ○ | ○ |
| Specimen 2 | ○ | ○ | ○ | ○ |
| Specimen 3 | ○ | ○ | ○ | ○ |
| Specimen 4 | △ | △ | ○ | ○–△ |
| Specimen 5 | ○ | △ | ○ | ○ |

(Note) the specimens in GROUP I are made of normal isobutylene-isoprene rubber, and those in GROUP II are made of chlorinated isobutylene-isoprene rubber. Time I is before sterilization, and Time II is after sterilization.

It will be appreciated from Table 3, that specimens 1 and 5 in Group I and specimen 4 in Group II suffers a slight reduction in the fit after sterilization but it is negligible, In general, the fit depends upon the material, hardness, the elasticity of the gasket, and also upon the stress to which the gasket 3 and plunger 2 are subjected in the process of fabrication. The fit differs depending upon the diameter of the tubular body 1. Repeated tests have demonstrated that the ranges of compressibility (C) and the product (C×S) of compressibility and contact area shown in Table 2 are optimal for enabling the gasket 3 and plunger 2 to fit in the tubular body 1.

In order to examine how the slidability of the gaskets and plunger change over a period of storage after sterilization, the specimens 4 and 5 in Group II were tested at the initial pressure which was required to start the plunger 2 by means of the push rod 2a. This examination was periodically conducted for several months from the initial sterilization. The gaskets 3 and plunger 2 remained inside the tubular body 1 at 40° C. through the period of examination (six months) so as to avoid any infliction of ambient influence. The results are shown in FIG. 8. The initial pressure is expressed in Kg/cm$^2$ in terms of force applied to a unit area of the cross-section perpendicular to the axis of the tubular body 1. It will be appreciated from FIG. 8 that the initial pressure was about 1 Kg/cm$^2$ at the start, about 1.4 Kg/cm$^2$ in two months, and finally about 1.6 to 1.7 Kg/cm$^2$. It is noticeable that the initial pressure required increases as the storage is prolonged but it remains within the range of 1 to 2 Kg/cm$^2$, which is not to such a degree as to reduce the slidability of the specimens 4 and 5.

What is claimed is:

1. An apparatus comprising:

a tubular body having an inside wall, an inside space, a front open end, a rear open end and an inside diameter r;

a front gasket slidable in said tubular body, said front gasket separating said inside space into a front compartment and a rear compartment, and each of said compartments having a substance therein;

a rear gasket that is capable of being connected to a push rod so as to function as a plunger, said front gasket being slidable in said tubular body in response to sliding of said rear gasket in said tubular body;

a bypass located between said front gasket and said front open end, said bypass having an axial length along said tubular body, and said bypass permitting the substance in said rear compartment to be introduced into said front compartment;

wherein said front gasket comprises a first front gasket arranged on the rear side of said bypass and a second front gasket arranged behind said first front gasket, said first and second front gaskets being axially slidable independently of each other upon sliding of said rear gasket in said tubular body by the push rod;

wherein said first and second front gaskets have a combined axial thickness less than said axial length of said bypass such that, when said first and second front gaskets are slid to said bypass, the substance in said rear compartment can be introduced into said front compartment through said bypass;

wherein each of said front and rear gaskets has at least two annular ribs sealingly engaging said inside wall of tubular body;

wherein each said annular rib has an uncompressed outside diameter R; and wherein said front and rear gaskets are disposed in said tubular body such that a compressibility C (%) of said ribs, defined as C (%)=(R−r)/R×100, is in a range of 2% to 10%, inclusive, and the product of the compressibility and the contact area (mm$^2$) of said ribs with said inside wall of said tubular body is within a range of 150 to 400.

2. The apparatus of claim 1, and further comprising a cap having an injection needle, said cap being secured to said front open end of said tubular body.

3. The apparatus of claim 1, wherein the product of the compressibility (%) and the whole contact area (mm$^2$) of said annular ribs of all of said front and rear gaskets is within a range of 300 to 1,200.

4. An apparatus comprising:

a tubular body having an inside wall, an inside space, a front open end, a rear open end and an inside diameter r;

a front gasket slidable in said tubular body, said front gasket separating said inside space into a front compartment and a rear compartment, and each of said components having a substance therein;

a rear gasket that is capable of being connected to a push rod so as to function as a plunger, said front gasket being slidable in said tubular body in response to sliding of said rear gasket in said tubular body;

a bypass located between said front gasket and said front open end, said bypass having an axial length along said tubular body, and said bypass permitting the substance in said rear compartment to be introduced into said front compartment;

wherein said front gasket comprises a first front gasket arranged on the rear side of said bypass and a second front gasket arranged behind said first front gasket, said first and second front gaskets being axially slidable independently of each other upon sliding of said rear gasket in said tubular body by the push rod;

wherein said first and second front gaskets have a combined axial thickness less than said axial length of said bypass such that, when said first and second front gaskets are slid to said bypass, the substance in said rear compartment can be introduced into said front compartment through said bypass;

wherein each of said front and rear gaskets comprises annular ribs having a space therebetween and bridging ribs extending between said annular ribs and subdividing said space between said annular ribs, said annular and bridging ribs sealingly engaging said inside wall of tubular body;

wherein each said rib has an uncompressed outside diameter R; and wherein said front and rear gaskets are disposed in said tubular body such that a compressibility C (%) of said ribs, defined as C (%)=(R−r)/R×100, is a range of 2% to 10%, inclusive, and the product of the compressibility and the contact area (mm$^2$) of said ribs with said inside wall of said tubular body is within a range of 150 to 400.

5. The apparatus of claim 1, and further comprising a cap having an injection needle, said cap being secured to said front open end of said tubular body.

6. The apparatus of claim 4, wherein the product of the compressibility (%) and the whole contact area (mm$^2$) of the annular ribs of all the gaskets is within a range of 300 to 1,200.

7. An apparatus comprising:

a tubular body having an inside wall, an inside space, a front open end, a rear open end and an inside diameter r;

a front gasket slidable in said tubular body, said front gasket separating said inside space into a front compartment and rear compartment, and each of said compartments having a substance therein;

a rear gasket in said tubular body, said front gasket being slidable in said tubular body in response to sliding of said rear gasket in said tubular body;

a bypass located between said front gasket and said front open end, said bypass having an axial length along said tubular body, and said bypass permitting the substance in said rear compartment to be introduced into said front compartment;

wherein said front gasket comprises a first front gasket arranged on the rear side of said bypass and a second front gasket arranged behind said first front gasket, said first and second front gaskets being axially slidable independently of each other upon sliding of said rear gasket in said tubular body by the push rod;

wherein said first and second front gaskets have a combined axial thickness less than said axial length of said bypass such that, when said first and second front gaskets are slid to said bypass, the substance in said rear compartment can be introduced into said front compartment through said bypass;

wherein each of said front and rear gaskets comprises a rib sealingly engaging said inside wall of tubular body;

wherein each said rib has an uncompressed outside diameter R; and wherein said front and rear gaskets are disposed in said tubular body such that a compressibility C (%) of said ribs, defined as C (%)=(R−r)/R×100, is in a range of 2% to 10%, inclusive, and the product of the compressibility and the contact area (mm$^2$) of said ribs with said inside wall of said tubular body is within a range of 150 to 400.

8. The apparatus of claim 7, and further comprising a cap having an injection needle, said cap being secured to said front open end of said tubular body.

9. The apparatus of claim 7, wherein said ribs of said front and rear gaskets comprise annular ribs having a space therebetween and bridging ribs extending between said annular ribs and subdividing said space between said annular ribs, said annular and bridging ribs sealingly engaging said inside wall of tubular body.

10. The apparatus of claim 7, wherein the product of the compressibility (%) and the whole contact area (mm$^2$) of the annular ribs of all the gaskets is within a range of 300 to 1,200.

* * * * *